(12) United States Patent
Bartley et al.

(10) Patent No.: US 9,309,478 B2
(45) Date of Patent: Apr. 12, 2016

(54) LUBRICATING COMPOSITION CONTAINING METAL CARBOXYLATE

(75) Inventors: Stuart L. Bartley, Wickliffe, OH (US); Mark R. Baker, Lyndhurst, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 38 days.

(21) Appl. No.: 13/122,422

(22) PCT Filed: Oct. 21, 2009

(86) PCT No.: PCT/US2009/061408
§ 371 (c)(1),
(2), (4) Date: May 5, 2011

(87) PCT Pub. No.: WO2010/048244
PCT Pub. Date: Apr. 29, 2010

(65) Prior Publication Data
US 2011/0207635 A1 Aug. 25, 2011

Related U.S. Application Data

(60) Provisional application No. 61/107,811, filed on Oct. 23, 2008.

(51) Int. Cl.
| | | |
|---|---|---|
| C10M 159/22 | (2006.01) | |
| B01F 17/00 | (2006.01) | |
| C10L 1/30 | (2006.01) | |
| C10M 129/32 | (2006.01) | |
| C07C 51/41 | (2006.01) | |
| C10M 129/40 | (2006.01) | |
| C10M 129/42 | (2006.01) | |
| C10M 141/08 | (2006.01) | |
| C10M 141/10 | (2006.01) | |

(52) U.S. Cl.
CPC ............ *C10M 129/32* (2013.01); *C07C 51/412* (2013.01); *C10M 129/40* (2013.01); *C10M 129/42* (2013.01); *C10M 141/08* (2013.01); *C10M 141/10* (2013.01); *C10M 2207/121* (2013.01); *C10M 2207/126* (2013.01); *C10M 2207/127* (2013.01); *C10M 2219/022* (2013.01); *C10M 2219/08* (2013.01); *C10M 2219/106* (2013.01); *C10M 2223/043* (2013.01); *C10N 2220/028* (2013.01)

(58) Field of Classification Search
CPC .................. C10M 129/04; C10M 2207/10
USPC .......................... 508/187, 320, 460
See application file for complete search history.

(56) References Cited

U.S. PATENT DOCUMENTS

| | | | |
|---|---|---|---|
| 3,284,409 A | 11/1966 | Casper | |
| 3,825,495 A | 7/1974 | Newingham et al. | |
| 4,180,466 A | 12/1979 | Newingham et al. | |
| 4,308,154 A * | 12/1981 | Clason et al. ................. | 508/369 |
| 4,459,215 A | 7/1984 | Salentine | |
| 5,487,838 A | 1/1996 | Luciani et al. | |
| 5,547,596 A | 8/1996 | Omiya | |
| 5,736,491 A * | 4/1998 | Patel et al. .................... | 508/365 |
| 6,294,507 B1 * | 9/2001 | Dahl .............................. | 508/459 |
| 6,528,458 B1 * | 3/2003 | Tagliamonte et al. ......... | 508/185 |
| 2001/0044391 A1 * | 11/2001 | Shiga et al. ................... | 508/378 |
| 2002/0086802 A1 * | 7/2002 | Cain ............................ | 508/185 |
| 2002/0119895 A1 | 8/2002 | Cook et al. | |
| 2004/0167041 A1 * | 8/2004 | Arimoto ....................... | 508/272 |
| 2010/0323935 A1 | 12/2010 | Baker et al. | |

FOREIGN PATENT DOCUMENTS

| | | |
|---|---|---|
| EP | 0399764 | 11/1990 |
| EP | 0770669 | 5/1997 |
| EP | 1803796 | 7/2007 |
| GB | 2293389 | 3/1996 |
| WO | 96/37585 | 11/1996 |

OTHER PUBLICATIONS

Corresponding PCT Publication WO 2010/048244 A1 and Search Report published Apr. 29, 2010.
Written Opinion from corresponding international Application No. PCT/US2009/061408 mailed Feb. 24, 2010.

* cited by examiner

*Primary Examiner* — Prem C Singh
*Assistant Examiner* — Francis C Campanell
(74) *Attorney, Agent, or Firm* — Deron A. Cook, Esq.; Teresan W. Gilbert, Esq.

(57) ABSTRACT

The invention relates to a lubricating composition comprising (a) at least 0.05 wt % of a non-aromatic metal carboxylate, wherein the metal carboxylate is derived from a branched carboxylic acid, and (b) an oil of lubricating viscosity. The invention further provides for the use of the lubricating composition for lubricating a limited slip differential.

7 Claims, No Drawings

LUBRICATING COMPOSITION CONTAINING METAL CARBOXYLATE

FIELD OF INVENTION

The invention relates to a lubricating composition comprising (a) at least 0.05 wt % of a non-aromatic metal carboxylate, wherein the metal carboxylate is derived from a branched carboxylic acid, and (b) an oil of lubricating viscosity. The invention further provides for the use of the lubricating composition for lubricating a limited slip differential.

BACKGROUND OF THE INVENTION

A limited slip differential in a vehicle typically employs a wet multi-plate clutch, i.e., clutch plates are immersed in a lubricant. The limited slip differential typically has bevel gear or spur gear planetary systems which distribute the drive torque evenly to the two driving wheels irrespective of their rotational speed. This makes it possible for the driven wheels to roll during cornering without slip between the wheel and road surface in spite of their different rotational speed. In order for the slip to be controlled lubricants containing compounds capable of improving friction performance, dispersants and sulphur- and/or phosphorus-containing extreme pressure agents may be used. Examples of lubricants of this type are disclosed in U.S. Pat. Nos. 4,308,154; 5,547,586; 4,180,466; 3,825,495; and European Patent Application 0 399 764 A1.

Lubricants containing compounds suitable for (i) deposit control (U.S. Pat. No. 3,284,409), and (ii) wear performance are described in International Application WO 96/037585, US Patent Application 2002/0119895, and U.S. Pat. No. 5,487,838.

SUMMARY OF THE INVENTION

The inventors of this invention have discovered that a lubricating composition and method as disclosed herein is capable of providing an acceptable level of at least one of (i) lubricant thermal stability, (ii) lubricant oxidative stability, (iii) high static coefficient of friction, (iv) fuel economy, (v) deposit control, (vi) seal compatibility, and (vii) low tendency towards noise, vibration and harshness (NVH) often manifested as chatter (i.e. an abnormal noise typically referred to as a low-frequency "growl" and "groan", particularly during higher-speed cornering manoeuvres). The inventors have also unexpectedly discovered that the lubricant composition and method disclosed herein may also be suitable for limited slip systems having one or more distinct plate materials. For example the plate materials may be steel, paper, ceramic, carbon fibers and systems employing a mixture of plate types such as steel on ceramic, carbon fibers in paper or steel on paper.

In one embodiment, the invention provides a lubricating composition comprising (a) at least 0.05 wt % of a non-aromatic metal carboxylate, wherein the metal carboxylate is derived from a branched carboxylic acid, and (b) an oil of lubricating viscosity.

In one embodiment, the invention provides a method of lubricating a limited slip differential comprising supplying to the limited slip differential a lubricating composition comprising (a) at least 0.05 wt % of a non-aromatic metal carboxylate, wherein the metal carboxylate is derived from a branched carboxylic acid, and (b) an oil of lubricating viscosity.

In one embodiment, the invention provides for the use of a lubricating composition comprising (a) at least 0.05 wt % of a non-aromatic metal carboxylate, wherein the metal carboxylate is derived from a branched carboxylic acid, and (b) an oil of lubricating viscosity. in a limited slip differential to provide an acceptable level of at least one of (i) lubricant thermal stability, (ii) lubricant oxidative stability, (iii) friction coefficients, (iv) fuel economy, (v) deposit control, (vi) seal compatibility, and (vii) chattering (abnormal noise).

In one embodiment the invention provides a lubricating composition comprising (a) at least 0.05 wt % of a non-aromatic metal carboxylate, wherein the metal carboxylate is derived from a carboxylic acid esterified with a alcohol having 4 to 16 carbon atoms, (b) an amine salt of a phosphoric acid ester, and (c) an oil of lubricating viscosity.

In one embodiment, the invention provides a lubricating composition comprising (a) at least 0.05 wt % of a non-aromatic metal carboxylate, wherein the metal carboxylate is derived from a branched carboxylic acid, and (b) an oil of lubricating viscosity.

In one embodiment, the invention provides a method of lubricating a limited slip differential comprising supplying to the limited slip differential a lubricating composition comprising (a) at least 0.05 wt % of a non-aromatic metal carboxylate, wherein the metal carboxylate is derived from a branched carboxylic acid, and (b) an oil of lubricating viscosity.

In one embodiment, the invention provides for the use of a lubricating composition comprising (a) at least 0.05 wt % of a non-aromatic metal carboxylate, wherein the metal carboxylate is derived from a branched carboxylic acid, and (b) an oil of lubricating viscosity in a limited slip differential to provide an acceptable level of at least one of (i) lubricant thermal stability, (ii) lubricant oxidative stability, (iii) friction coefficients, (iv) fuel economy, (v) deposit control, (vi) seal compatibility, and (vii) chattering (abnormal noise).

DETAILED DESCRIPTION OF THE INVENTION

The present invention provides a lubricating composition and method as disclosed herein above.

Metal Carboxylate

The lubricating composition of the present invention includes a non-aromatic metal carboxylate, wherein the metal carboxylate is derived from a branched carboxylic acid.

The metal carboxylate may be derived from known reactions including salting of a branched carboxylic acid with a metal.

The metal may be a monovalent, divalent, trivalent, or mixtures thereof. The metal of the metal carboxylate may be an alkali metal, an alkaline earth metal, or a transition metal (typically from the $4^{th}$ period (i.e., scandium to zinc)), or mixtures thereof.

In one embodiment the metal of the metal carboxylate may be an alkaline earth metal, or a transition metal (typically from the $4^{th}$ period). Examples of a suitable metal include sodium, lithium, calcium, magnesium, copper, zinc, or mixtures thereof. In one embodiment the metal is zinc or copper. In one embodiment the metal is zinc.

The carboxylic acid of the present invention is a branched carboxylic acid. The carboxylic acid may have any degree of branching, and branching at any position along the carboxylic acid carbon chain. Typically the carboxylic acid may be a branched carboxylic acid, wherein the branching occurs on the alpha or beta carbon.

In one embodiment the branched carboxylic acid may be branched at the alpha carbon.

In one embodiment the branched carboxylic acid may be branched at the beta carbon.

The branched carboxylic acid may have 4 to 20, or 6 to 14, or 6 to 12 carbon atoms.

The branched carboxylic acid may have two or more branches. When the branched carboxylic acid has 2 branches, the longest carbon chain in the molecule including the branching group and the carbon atoms of the carboxylic group may contain 2 to 19, 4 to 19, or 4 to 10 carbon atoms. For instance 2-ethylhexanoic acid has a longest carbon chain length of 6 carbon atoms, and 2-methylhexanoic acid has a longest chain length of 6 carbon atoms.

The branched carboxylic acid may have two or more branches. When the branched carboxylic acid has 2 branches, the shortest carbon chain after the branching carbon may contain 2 to 18, or 2 to 10 carbon atoms. For instance 2-ethylhexanoic acid has a shortest carbon chain length of 2 carbon atoms (i.e, the ethyl group), and 2-methylhexanoic acid has a shortest chain length of 1 carbon atom (i.e., the methyl group). Typically the number of carbon atoms of the shortest carbon chain may be at least 1 or at least 2 carbon atoms less than the number of carbon atoms of the longest carbon chain in the molecule including the branching group and the carbon atoms of the carboxylic group.

Examples of a suitable carboxylic acid include 2-ethylhexanoic acid, iso-tridecanoic acid, iso-decanoic acid, iso-stearic acid, iso-butyric acid, 2-methypropanoic acid, 2-ethylbutyric acid, 2-methylhexanoic acid, dimer or trimer acids of either oleic acid or tall oil fatty acid (prepared in the presence of a iron catalyst (commercially sold under the Tradename of Pripol® by Uniquema), or mixtures thereof. In one embodiment the carboxylic acid may be 2-ethylhexanoic acid.

The metal carboxylate may be either neutral, basic or mixtures thereof. In one embodiment the metal carboxylate may be a basic metal carboxylate, such as, a calcium, magnesium, copper or zinc carboxylate. In one embodiment the metal of the metal carboxylate may be copper or zinc. A basic metal carboxylate may have a structure including (R—COO)M-OH, or (R—COO)M-O-M(OOC—R), wherein the R—COO represents the branched carboxylic acid moiety (and the branched carboxylic acid is described above), M represents calcium, magnesium, copper, or zinc. M is believed to be ionically bonded to R—COO. When the metal is zinc, the formula of the basic compound may be $(RCO_2)_6Zn_4O$ or $[(RCO_2)_2Zn]_3ZnO$ (both structures being 100% basic compound of zinc carboxylate). The structures of $(RCO_2)_6Zn_4O$ or $[(RCO_2)_2Zn]_3ZnO$ are believed to have zinc in a tetrahedral structure.

Typically, the metal carboxylate may be a basic metal carboxylate containing at least 50 wt %, or at least 60 wt % of the metal carboxylate having the basic structure.

The metal carboxylate may be present in the lubricating composition in an amount in the range of 0.1 wt % to 5 wt %, or 0.2 wt % to 3 wt %, or greater than 0.2 wt % to 3 wt %, or 0.5 wt % to 3 wt %, or 0.5 wt % to 2.5 wt % of the lubricating composition.

Borated Phospholipid

Optionally the lubricating composition further includes a borated phospholipid. In one embodiment the lubricating composition includes a borated phospholipid. In one embodiment the lubricating composition does not contain a borated phospholipid.

The phospholipid may be any lipid containing a phosphoric acid group, such as lecithin or cephalin, or derivatives thereof. Examples of phospholipids include phosphatidylcholine, phosphatidylserine, phosphatidylinositol, phosphatidylethanolamine, phosphotidic acid and mixtures thereof. The phospholipids may be glycerophospholipids, glycerol derivatives of the above list of phospholipids. Typically, the glycerophospholipids have one or two acyl, alkyl or alkenyl groups on a glycerol residue. The alkyl or alkenyl groups may contain 8 to 30, or 8 to 25, or 12 to 24 carbon atoms. Examples of suitable alkyl or alkenyl groups include octyl, dodecyl, hexadecyl, octadecyl, docosanyl, octenyl, dodecenyl, hexadecenyl and octadecenyl. In one embodiment the phospholipid is lecithin, or derivatives thereof.

Derivatives of phospholipids may be acylated or hydroxylated phospholipids. For example, lecithin as well as acylated and hydroxylated lecithins may be used in the present invention. Acylated lecithins may be prepared by reacting an acylating agent with a lecithin. Acylating agents include acetic acid. An example of a commercially available acylated lecithin is Thermolec 200™ acylated soya lecithin (available from Ross & Rowe, Inc. of Decatur, Ill.). Hydroxylated lecithins may also be used. Hydroxylated lecithins may be prepared by acidic or enzymatic hydrolysis. An example of hydroxylated lecithins is Thermolec 1018™ hydroxylated lecithin commercially available from Ross & Rowe, Inc.

Phospholipids and lecithins are described in detail in Encyclopedia of Chemcial Technology, Kirk and Othmer, 3rd Edition, in "Fats and Fatty Oils", Volume 9, pages 795-831 and in "Lecithins", Volume 14, pages 250-269.

Boronation of the phospholipids may be carried out by reaction with boron compounds. The boron compounds include boron oxide, boron oxide hydrate, boron trioxide, boron trifluoride, boron tribromide, boron trichloride, boron acids such as boronic acid (i.e., alkyl-$B(OH)_2$ or aryl-$B(OH)_2$), boric acid (i.e., $H_3BO_3$), tetraboric acid (i.e., $H_2B_4O_7$), metaboric acid (i.e., $HBO_2$), boron anhydrides, boron amides and various esters of such boron acids.

Borated phospholipids suitable for the lubricating composition are described in more detail in U.S. Patent Application 60/992,738 (filed Dec. 6, 2007 by Baker and Rhoads), paragraphs [0014] to [0024] of the provisional application.

A more detailed description and methods of preparation of borated phospholipids is described in U.S. Pat. No. 5,487,838. Examples 1 to 7 as disclosed in column 20 line 64 to column 22 line 51 of U.S. Pat. No. 5,487,838 exemplify the preparation borated phospholipids.

The borated phospholipid may be present at 0 wt %, 5 to 6 wt %, or 0.05 wt % to 6 wt %, or 0.5 wt % to 3 wt % of the lubricating composition.

Amine Salt of a Phosphoric Acid Ester

In one embodiment the lubricating composition further includes an amine salt of a phosphoric acid ester. The phosphoric acid utilised to prepare the phosphoric acid ester amine salt may be either a phosphoric acid, or a thiophosphoric acid.

The amine salt of a phosphoric acid ester may contain ester groups each having 1 to 30, 6 to 30, 8 to 30, 10 to 24 or 12 to 20, or 16 to 20 carbon atoms, with the proviso that a portion or all of ester groups are sufficiently long to solubilise the amine salt of a phosphoric acid ester in an oil of lubricating viscosity. Typically ester groups containing 4 or more carbon atoms are particularly useful.

Examples of suitable ester groups include isopropyl, methyl-amyl (may also be referred to as 1,3-dimethyl butyl), 2-ethylhexyl, heptyl, octyl, nonyl, decyl, dodecyl, butadecyl, pentadecyl, hexadecyl, heptadecyl, octadecyl, nonadecyl, eicosyl, or mixtures thereof.

In one embodiment the ester groups are selected from the group consisting of isopropyl, methyl-amyl (may also be referred to as 1,3-dimethyl butyl), 2-ethylhexyl, heptyl, octyl, nonyl, decyl, and mixtures thereof.

The amines which may be suitable for use as the amine salt include primary amines, secondary amines, tertiary amines, and mixtures thereof. The amines include those with at least one hydrocarbyl group, or, in certain embodiments, two or three hydrocarbyl groups. The hydrocarbyl groups may contain 2 to 30 carbon atoms, or in other embodiments 8 to 26, or 10 to 20, or 13 to 19 carbon atoms.

Primary amines include ethylamine, propylamine, butylamine, 2-ethylhexylamine, octylamine, and dodecylamine, as well as linear amines as n-octylamine, n-decylamine, n-dodecylamine, n-tetradecylamine, n-hexadecylamine, n-octadecylamine and oleyamine. Other useful fatty amines include commercially available fatty amines such as "Armeen®" amines (products available from Akzo Chemicals, Chicago, Ill.), such as Armeen C, Armeen O, Armeen OL, Armeen T, Armeen HT, Armeen S and Armeen SD, wherein the letter designation relates to the fatty group, such as coco, oleyl, tallow, or stearyl groups.

Examples of suitable secondary amines include dimethylamine, diethylamine, dipropylamine, dibutylamine, diamylamine, dihexylamine, diheptylamine, methylethylamine, ethylbutylamine, ethylamylamine, dicocoamine and di-2-ethylhexylamine. The secondary amines may be cyclic amines such as piperidine, piperazine and morpholine.

The amine may also be a tertiary-aliphatic primary amine. The aliphatic group in this case may be an alkyl group containing 2 to 30, or 6 to 26, or 8 to 24 carbon atoms. Tertiary alkyl amines include monoamines such as tert-butylamine, tert-hexylamine, 1-methyl-1-amino-cyclohexane, tert-octylamine, tert-decylamine, tertdodecylamine, tert-tetradecylamine, tert-hexadecylamine, tert-octadecylamine, tert-tetracosanylamine, and tert-octacosanylamine.

The amine salt of a phosphorus acid ester may be a reaction product of a $C_{12-20}$ alkyl phosphoric acid with a tertiary $C_{11-22}$ alkyl primary amine.

In one embodiment the amine salt of a phosphorus acid ester includes an amine with C11 to C14 tertiary alkyl primary groups or mixtures thereof. In one embodiment the amine salt of a phosphorus compound includes an amine with C14 to C18 tertiary alkyl primary amines or mixtures thereof. In one embodiment the amine salt of a phosphorus compound includes an amine with C18 to C22 tertiary alkyl primary amines or mixtures thereof.

In one embodiment the amine salt of a phosphorus acid ester includes the reaction product of octadecenyl phosphoric acid with Primene 81R™.

Mixtures of amines may also be used in the invention. In one embodiment a useful mixture of amines is "Primene™ 81R" and "Primene™ JMT." Primene™ 81R and Primene™ JMT (both produced and sold by Rohm & Haas) are mixtures of C11 to C14 tertiary alkyl primary amines and C18 to C22 tertiary alkyl primary amines respectively.

In one embodiment the amine salt of a phosphorus acid ester is the reaction product of a C14 to C18 alkylated phosphoric acid with Primene 81R™ (produced and sold by Rohm & Haas) which is a mixture of C11 to C14 tertiary alkyl primary amines.

Examples of the amine salt of a phosphorus acid ester include the reaction product(s) of isopropyl, methyl-amyl (1,3-dimethyl butyl or mixtures thereof), 2-ethylhexyl, heptyl, octyl, nonyl or decyl dithiophosphoric acids with ethylene diamine, morpholine, or Primene 81R™, and mixtures thereof.

Examples of the amine salt of a phosphorus acid ester include the reaction product(s) of tetraadecyl, pentadecyl, hexadecyl, heptadecyl, octadecyl, nonadecyl or eicosyl dithiophosphoric acids with ethylene diamine, morpholine, or Primene 81R™, and mixtures thereof. In one embodiment the amine salt of a phosphorus acid ester includes the reaction product of octadecenyl dithiophosphoric acid with Primene 81R™.

In one embodiment the amine salt of a phosphorus compound may be a sulphur-free phosphorus-containing compound of an amine salt of either (i) a hydroxy-substituted di-ester of phosphoric acid, or (ii) a phosphorylated hydroxy-substituted di- or tri-ester of phosphoric acid. A more detailed description of this type of compound is described in more detail in International Publication WO 2008/094759.

In one embodiment the amine salt of a phosphoric acid is a compound described in U.S. Pat. No. 3,197,405. In one embodiment the amine salt of a phosphorus compound other than those disclosed above, may be prepared by any one of examples 1 to 25 of U.S. Pat. No. 3,197,405.

In one embodiment the amine salt of a phosphorus compound other than those disclosed above, is a reaction product prepared from a dithiophosphoric acid is reacting with an epoxide or a glycol. This reaction product is further reacted with a phosphorus acid, anhydride, or lower ester (where "lower" signifies 1 to 8, or 1 to 6, or 1 to 4, or 1 to 2 carbon atoms in the alcohol-derived portion of the ester). The epoxide includes an aliphatic epoxide or a styrene oxide. Examples of useful epoxides include ethylene oxide, propylene oxide, butene oxide, octene oxide, dodecene oxide, styrene oxide and the like. In one embodiment the epoxide is propylene oxide. The glycols include aliphatic glycols having 1 to 12, or 2 to 6, or 2 to 3 carbon atoms. The dithiophosphoric acids, glycols, epoxides, inorganic phosphorus reagents and methods of reacting the same are described in U.S. Pat. Nos. 3,197,405 and 3,544,465. The resulting acids are then salted with amines.

An example of suitable dithiophosphoric acid based product is prepared by adding phosphorus pentoxide (about 64 grams) at 58° C. over a period of 45 minutes to 514 grams of hydroxypropyl O,O-di(1,3-dimethylbutyl)phosphorodithioate (prepared by reacting di(1,3-dimethylbutyl)-phosphorodithioic acid with 1.3 moles of propylene oxide at 25° C.). The mixture is heated at 75° C. for 2.5 hours, mixed with a diatomaceous earth and filtered at 70° C. The filtrate contains 11.8% by weight phosphorus, 15.2% by weight sulphur, and an acid number of 87 (bromophenol blue).

The amine salt of a phosphorus acid ester may be present at 0 wt % to 5 wt %, or 0.01 wt % to 5 wt %, or 0.01 wt % to 2 wt %, or 0.25 wt % to 1 wt % of the lubricating composition.

Oils of Lubricating Viscosity

The lubricating composition comprises an oil of lubricating viscosity. Such oils include natural and synthetic oils, oil derived from hydrocracking, hydrogenation, and hydrofinishing, unrefined, refined and re-refined oils and mixtures thereof.

Unrefined oils are those obtained directly from a natural or synthetic source generally without (or with little) further purification treatment.

Refined oils are similar to the unrefined oils except they have been further treated in one or more purification steps to improve one or more properties. Purification techniques are known in the art and include solvent extraction, secondary distillation, acid or base extraction, filtration, percolation and the like.

Re-refined oils are also known as reclaimed or reprocessed oils, and are obtained by processes similar to those used to obtain refined oils and often are additionally processed by techniques directed to removal of spent additives and oil breakdown products.

Natural oils useful in making the inventive lubricants include animal oils (e.g., lard oil), vegetable oils (e.g., castor oil), mineral lubricating oils such as liquid petroleum oils and solvent-treated or acid-treated mineral lubricating oils of the paraffinic, naphthenic or mixed paraffinic-naphthenic types and oils derived from coal or shale or mixtures thereof.

Synthetic lubricating oils are useful and include hydrocarbon oils such as polymerised and interpolymerised olefins (e.g., polybutylenes, polypropylenes, propyleneisobutylene copolymers); poly(1-hexenes), poly(1-octenes), poly(1-decenes), and mixtures thereof; alkyl-benzenes (e.g. dodecylbenzenes, tetradecylbenzenes, dinonylbenzenes, di-(2-ethylhexyl)-benzenes); polyphenyls (e.g., biphenyls, terphenyls, alkylated polyphenyls); alkylated diphenyl ethers and alkylated diphenyl sulphides and the derivatives, analogs and homologs thereof or mixtures thereof.

Other synthetic lubricating oils include polyol esters (such as Priolube®3970), diesters, liquid esters of phosphorus-containing acids (e.g., tricresyl phosphate, trioctyl phosphate, and the diethyl ester of decane phosphonic acid), or polymeric tetrahydrofurans. Synthetic oils may be produced by Fischer-Tropsch reactions and typically may be hydroisomerised Fischer-Tropsch hydrocarbons or waxes. In one embodiment oils may be prepared by a Fischer-Tropsch gas-to-liquid synthetic procedure as well as other gas-to-liquid oils.

Oils of lubricating viscosity may also be defined as specified in the American Petroleum Institute (API) Base Oil Interchangeability Guidelines. The five base oil groups are as follows: Group I (sulphur content>0.03 wt %, and/or <90 wt % saturates, viscosity index 80-120); Group II (sulphur content≤0.03 wt %, and ≥90 wt % saturates, viscosity index 80-120); Group III (sulphur content≤0.03 wt %, and ≥90 wt % saturates, viscosity index≥120); Group IV (all polyalphaolefins (PAOs)); and Group V (all others not included in Groups I, II, III, or IV). The oil of lubricating viscosity includes an API Group I, Group II, Group III, Group IV, Group V oil or mixtures thereof. Often the oil of lubricating viscosity is an API Group I, Group II, Group III, Group IV oil or mixtures thereof. Alternatively the oil of lubricating viscosity is often an API Group II, Group III or Group IV oil or mixtures thereof.

The amount of the oil of lubricating viscosity present is typically the balance remaining after subtracting from 100 wt % the sum of the amount of the borated phospholipid, the amine salt of a phosphoric acid ester, and the other performance additives.

The lubricating composition may be in the form of a concentrate and/or a fully formulated lubricant. If the lubricating composition disclosed herein, is in the form of a concentrate (which may be combined with additional oil to form, in whole or in part, a finished lubricant), the ratio of the of components of the lubricating composition, to the oil of lubricating viscosity and/or to diluent oil include the ranges of 1:99 to 99:1 by weight, or 80:20 to 10:90 by weight. When in the form of a concentrate, the present invention may be part of a full lubricant composition, or may be a supplemental additive package or "top treat".

Other Performance Additives

The composition of the invention optionally further includes at least one other performance additive. The other performance additives include dispersants, metal deactivators, detergents, viscosity modifiers, extreme pressure agents (typically boron- and/or sulphur- and/or phosphorus-containing), antiwear agents, antioxidants (such as hindered phenols, aminic antioxidants or molybdenum compounds), corrosion inhibitors, foam inhibitors, demulsifiers, pour point depressants, seal swelling agents, friction modifiers and mixtures thereof.

The total combined amount of the other performance additives (excluding the viscosity modifiers) present on an oil free basis may include ranges of 0 wt % to 25 wt %, or 0.01 wt % to 20 wt %, or 0.1 wt % to 15 wt % or 0.5 wt % to 10 wt %, or 1 to 5 wt % of the composition. Although one or more of the other performance additives may be present, it is common for the other performance additives to be present in different amounts relative to each other.

In one embodiment the lubricating composition is free of molybdenum-containing additives.

Viscosity Modifiers

In one embodiment the lubricating composition further includes one or more viscosity modifiers.

When present the viscosity modifier may be present in an amount of 0.5 wt % to 70 wt %, 1 wt % to 60 wt %, or 5 wt % to 50 wt %, or 10 wt % to 50 wt % of the lubricating composition.

Viscosity modifiers include (a) polymethacrylates, (b) esterified copolymers of (i) a vinyl aromatic monomer and (ii) an unsaturated carboxylic acid, anhydride, or derivatives thereof, (c) esterified interpolymers of (i) an alpha-olefin; and (ii) an unsaturated carboxylic acid, anhydride, or derivatives thereof, or (d) hydrogenated copolymers of styrene-butadiene, (e) ethylene-propylene copolymers, (f) polyisobutenes, (g) hydrogenated styrene-isoprene polymers, (h) hydrogenated isoprene polymers, or (i) mixtures thereof.

In one embodiment the viscosity modifier includes (a) a polymethacrylate, (b) an esterified copolymer of (i) a vinyl aromatic monomer; and (ii) an unsaturated carboxylic acid, anhydride, or derivatives thereof, (c) an esterified interpolymer of (i) an alpha-olefin; and (ii) an unsaturated carboxylic acid, anhydride, or derivatives thereof, or (d) mixtures thereof.

Extreme Pressure Agents

Extreme pressure agents include compounds containing boron and/or sulphur and/or phosphorus.

The extreme pressure agent may be present in the lubricating composition at 0 wt % to 20 wt %, or 0.05 wt % to 10 wt %, or 0.1 wt % to 8 wt % of the lubricating composition.

In one embodiment the extreme pressure agent is a sulphur-containing compound. In one embodiment the sulphur-containing compound may be a sulphurised olefin, a polysulphide, or mixtures thereof.

Examples of the sulphurised olefin include a sulphurised olefin derived from propylene, isobutylene, pentene; an organic sulphide and/or polysulphide including benzyldisulphide; bis-(chlorobenzyl)disulphide; dibutyl tetrasulphide; di-tertiary butyl polysulphide; and sulphurised methyl ester of oleic acid, a sulphurised alkylphenol, a sulphurised dipentene, a sulphurised terpene, a sulphurised Diels-Alder adduct, an alkyl sulphenyl N'N-dialkyl dithiocarbamates; or mixtures thereof. In one embodiment the sulphurised olefin includes a sulphurised olefin derived from propylene, isobutylene, pentene or mixtures thereof.

In one embodiment the extreme pressure agent sulphur-containing compound includes a dimercaptothiadiazole or derivative, or mixtures thereof. Examples of the dimercaptothiadiazole include 2,5-dimercapto-1,3,4-thiadiazole or a hydrocarbyl-substituted 2,5-dimercapto-1,3-4-thiadiazole, or oligomers thereof. The oligomers of hydrocarbyl-substituted 2,5-dimercapto-1,3-4-thiadiazole typically form by forming a sulphur-sulphur bond between 2,5-dimercapto-1,3,4-thiadiazole units to form derivatives or oligomers of two or more of said thiadiazole units. Suitable 2,5-dimercapto-1, 3,4-thiadiazole derived compounds include 2,5-bis(tert-nonyldithio)-1,3,4-thiadiazole or 2-tert-nonyldithio-5-mercapto-1,3,4-thiadiazole.

The number of carbon atoms on the hydrocarbyl substituents of the hydrocarbyl-substituted 2,5-dimercapto-1,3,4-thiadiazole typically include 1 to 30, or 2 to 20, or 3 to 16.

In one embodiment the extreme pressure agent includes a boron-containing compound. The boron-containing compound includes a borate ester (may also be referred to as a borated epoxide), a borate alcohol, a borated dispersant or mixtures thereof.

In one embodiment the boron-containing compound is a borate ester or a borate alcohol. The borate ester or borate alcohol compounds are substantially the same except the borate alcohol has at least one hydroxyl group that is not esterified. Therefore, as used herein the term "borate ester" is used to refer to either borate ester or borate alcohol.

The borate ester may be prepared by the reaction of a boron compound and at least one compound selected from epoxy compounds, halohydrin compounds, epihalohydrin compounds, alcohols and mixtures thereof. The alcohols include dihydric alcohols, trihydric alcohols or higher alcohols, with the proviso for one embodiment that hydroxyl groups are on adjacent carbon atoms i.e. vicinal. The term "epoxy compounds" is used when referring to "at least one compound selected from epoxy compounds, halohydrin compounds, epihalohydrin compounds and mixtures thereof."

Boron compounds suitable for preparing the borate ester include the various forms selected from the group consisting of boric acid (including metaboric acid, $HBO_2$, orthoboric acid, $H_3BO_3$, and tetraboric acid, $H_2B_4O_7$), boric oxide, boron trioxide and alkyl borates. The borate ester may also be prepared from boron halides.

In one embodiment suitable borate ester compounds include tripropyl borate, tributyl borate, tripentyl borate, trihexyl borate, triheptyl borate, trioctyl borate, trinonyl borate and tridecyl borate.

In one embodiment the borate ester compounds include tributyl borate, tri-2-ethylhexyl borate or mixtures thereof.

In one embodiment, the boron-containing compound is a borated dispersant, typically derived from an N-substituted long chain alkenyl succinimide. In one embodiment the borated dispersant includes a polyisobutylene succinimide. Borated dispersant are described in more detail in U.S. Pat. No. 3,087,936; and U.S. Pat. No. 3,254,025.

In one embodiment the borated dispersant is used in combination with a sulphur-containing compound or a borated ester.

In one embodiment the extreme pressure agent is other than a borated dispersant.

The number average molecular weight of the hydrocarbon from which the long chain alkenyl group was derived includes ranges of 350 to 5000, or 500 to 3000, or 550 to 1500. The long chain alkenyl group may have a number average molecular weight of 550, or 750, or 950 to 1000.

The N-substituted long chain alkenyl succinimides are borated using a variety of agents including boric acid (for example, metaboric acid, $HBO_2$, orthoboric acid, $H_3BO_3$, and tetraboric acid, $H_2B_4O_7$), boric oxide, boron trioxide, and alkyl borates. In one embodiment the borating agent is boric acid which may be used alone or in combination with other borating agents.

The borated dispersant may be prepared by blending the boron compound and the N-substituted long chain alkenyl succinimides and heating them at a suitable temperature, such as, 80° C. to 250° C., or 90° C. to 230° C., or 100° C. to 210° C., until the desired reaction has occurred. The molar ratio of the boron compounds to the N-substituted long chain alkenyl succinimides may have ranges including 10:1 to 1:4, or 4:1 to 1:3; or the molar ratio of the boron compounds to the N-substituted long chain alkenyl succinimides may be 1:2. An inert liquid may be used in performing the reaction. The liquid may include toluene, xylene, chlorobenzene, dimethylformamide or mixtures thereof.

Friction modifiers (other than (a) a borated phospholipid, and (b) an amine salt of a phosphoric acid ester) include fatty amines, esters such as borated glycerol esters, fatty phosphites, fatty acid amides, fatty epoxides, borated fatty epoxides, alkoxylated fatty amines, borated alkoxylated fatty amines, metal salts of fatty acids, or fatty imidazolines, condensation products of carboxylic acids and polyalkylene-polyamines.

In one embodiment the lubricating composition may contain phosphorus- or sulphur-containing antiwear agents other than compounds described as an extreme pressure agent of the amine salt of a phosphoric acid ester described above. Examples of the antiwear agent may include a non-ionic phosphorus compound (typically compounds having phosphorus atoms with an oxidation state of +3 or +5), a metal dialkyldithiophosphate (typically zinc dialkyldithiophosphates), a metal mono- or di-alkylphosphate (typically zinc phosphates), or mixtures thereof.

The non-ionic phosphorus compound includes a phosphite ester, a phosphate ester, or mixtures thereof. A more detailed description of the non-ionic phosphorus compound include column 9, line 48 to column 11, line 8 of U.S. Pat. No. 6,103,673.

In one embodiment the lubricating composition of the invention further includes a dispersant. The dispersant may be a succinimide dispersant (for example N-substituted long chain alkenyl succinimides), a Mannich dispersant, an ester-containing dispersant, a condensation product of a fatty hydrocarbyl monocarboxylic acylating agent with an amine or ammonia, an alkyl amino phenol dispersant, a hydrocarbyl-amine dispersant, a polyether dispersant or a polyetheramine dispersant.

In one embodiment the succinimide dispersant includes a polyisobutylene-substituted succinimide, wherein the polyisobutylene from which the dispersant is derived may have a number average molecular weight of 400 to 5000, or 950 to 1600.

Succinimide dispersants and their methods of preparation are more fully described in U.S. Pat. Nos. 4,234,435 and 3,172,892.

Suitable ester-containing dispersants are typically high molecular weight esters. These materials are described in more detail in U.S. Pat. No. 3,381,022.

In one embodiment the dispersant includes a borated dispersant. Typically the borated dispersant includes a succinimide dispersant including a polyisobutylene succinimide, wherein the polyisobutylene from which the dispersant is derived may have a number average molecular weight of 400 to 5000. Borated dispersants are described in more detail above within the extreme pressure agent description.

Dispersant viscosity modifiers (often referred to as DVMs) include functionalised polyolefins, for example, ethylene-propylene copolymers that have been functionalized with the reaction product of maleic anhydride and an amine, a polymethacrylate functionalised with an amine, or styrene-maleic anhydride copolymers reacted with an amine may also be used in the composition of the invention.

Corrosion inhibitors include 1-amino-2-propanol, octylamine octanoate, condensation products of dodecenyl succinic acid or anhydride and/or a fatty acid such as oleic acid with a polyamine.

Metal deactivators include derivatives of benzotriazoles (typically tolyltriazole), 1,2,4-triazoles, benzimidazoles, 2-alkyldithiobenzimidazoles or 2-alkyldithiobenzothiazoles. The metal deactivators may also be described as corrosion inhibitors.

Foam inhibitors include copolymers of ethyl acrylate and 2-ethylhexylacrylate and optionally vinyl acetate.

Demulsifiers include trialkyl phosphates, and various polymers and copolymers of ethylene glycol, ethylene oxide, propylene oxide, or mixtures thereof.

Pour point depressants including esters of maleic anhydride-styrene, polymethacrylates, polyacrylates or polyacrylamides.

Seal swell agents including Exxon Necton-37™ (FN 1380) and Exxon Mineral Seal Oil™ (FN 3200).

INDUSTRIAL APPLICATION

The limited slip differential typically incorporates a self-contained lubricant supply isolated from the lubricant disposed in the differential housing or carrier. The self-contained lubricant of the limited slip differential is generally different from the lubricant supplied to a manual transmission or an automatic transmission fluid. In both the manual and automatic transmission systems not comprising a limited slip differential one lubricant is sufficient to lubricate all of the transmission constituents.

The lubricating composition suitable for the limited slip differential may have a sulphur content in the range of 0.3 wt % to 5 wt %, or 0.5 wt % to 5 wt %, or 0.5 wt % to 3 wt % or 0.8 wt % to 2.5 wt %, or 1 wt % to 2 wt %.

In one embodiment the lubricating composition suitable for the limited slip differential is a fully formulated fluid.

In one embodiment the lubricating composition suitable for the limited slip differential is a top treat concentrate.

When the lubricating composition is in the form of a top treat concentrate, the concentrate may be added at 0.2 wt % to 10 wt %, or 0.5 wt % to 7 wt % relative to the amount of lubricant in a limited slip differential.

In one embodiment the lubricating composition consists of or consists essentially of (a) at least 0.05 wt % of a non-aromatic metal carboxylate, wherein the metal carboxylate is derived from a branched carboxylic acid, (b) an amine salt of a phosphoric acid ester, (c) an oil of lubricating viscosity, and optionally a viscosity modifier. Typically a lubricating composition of this type may be a top treat concentrate.

In one embodiment the lubricating composition consists of or consists essentially of (a) at least 0.05 wt % of a non-aromatic metal carboxylate, wherein the metal carboxylate is derived from a branched carboxylic acid, (b) an amine salt of a phosphoric acid ester, (c) an oil of lubricating viscosity, (d) a borated phospholipid, and optionally a viscosity modifier. Typically a lubricating composition of this type may be a top treat concentrate.

The following examples provide illustrations of the invention. These examples are non exhaustive and are not intended to limit the scope of the invention.

EXAMPLES

Preparative Example 1 (Prep1) is the preparation of zinc 2-ethylhexanoate. 1.5 moles of 2-ethylhexanoic acid and 0.2 g of 2,6-di-tertiary butyl cresol are added to a 4-neck flask equipped with a mechanical stirrer, nitrogen inlet, thermocouple and condenser. The flask is heated to 80° C. and then 1 mole of zinc oxide is added over a period of 90 minutes. The flask is then maintained at 80° C. for another 240 minutes. The condenser is removed and a goose-neck condenser added to remove distillate. Vacuum is applied and the temperature is increased to 150° C. and held for 40 minutes (thereby removing water). The flask is maintained at 150° C. for another 30 minutes before cooling to 100° C. The product is cooled and filtered through a Fax-5 filter. 254 g of a pale yellow liquid is obtained. The TBN of the product is 376.2 mg KOH per g of sample. The zinc content is between 22.5% and 23%.

Example 1 (EX1)

1271 g of a commercially available axle fluid is top-treated with 29.3 g of the product from Prep1.

The composition of EX1 is prepared by blending the axle fluid with Prep1 in a 4-neck flask equipped with overhead stirrer, thermocouple, condenser and air inlet. The exit port of the condenser has a series of caustic and bleach traps. The flask and contents are heated to 60° C. and held for 30 minutes. Air is applied and the flask is heated to 140° C. for 7 hours, followed by 8 hours at 150° C. Upon cooling a dark brown liquid is obtained.

Comparative Example 1 (CE1) is the same commercially available axle fluid as EX1, except the zinc 2-ethylhexanoate is not added, subjected to the same thermal stressing as EX1.

The examples prepared (EX1 and CE1) are evaluated using a mu-PVT (mu, friction coefficient obtained at varying Pressures, Velocities and Temperatures) friction screen test on a Low Speed SAE #2 test machine. This friction screen test utilises a Dana Model 80 plate configuration with Miba MC-631 friction material with the following plate configuration (S-F-S-F-S-F-S-F-S, where S is a steel plate, and F is a friction plate) thereby producing 8 active friction surfaces. The test runs through a map of varying apply pressures and plate differential speeds while holding the temperature constant at 50° C. There are six apply pressure settings of 190, 380, 570, 760, 950 and 1075 kPa. At each apply pressure setting, four distinct plate differential speeds of 15, 50, 85 and 120 rpm are utilised. At each plate differential speed, twenty five repeat cycles are conducted. Each test has a total of 600 cycles (six pressures×four speeds×twenty-five cycles). A 600 cycle mu-PVT or friction map is conducted before and after a durability cycle to assess the change in friction performance. The durability cycle consists of a constant apply pressure of 570 kPa at a fluid temperature of 80° C. and cycling the plate differential speed between 120 and 0 rpm. One complete cycle consists of 5 seconds at 0 rpm and 5 seconds at 120 rpm. This is repeated for a total of 2500 cycles. The primary measurement is an NVH rating that depicts the variation in the torque signal during each discrete speed event or the difference between the minimum and maximum friction coefficient obtained during the event. This measurement assigns a number to the magnitude of the torque signal variation according to the following table:

| Torque Signal Variation | NVH Rating |
|---|---|
| Between 0 and 0.02 Coefficient of Friction Units | 0 |
| Between 0.02 and 0.04 Coefficient of Friction Units | 1 |
| Between 0.04 and 0.06 Coefficient of Friction Units | 2 |
| Between 0.06 and 0.08 Coefficient of Friction Units | 3 |
| Between 0.08 and 0.10 Coefficient of Friction Units | 4 |
| Between 0.10 and 0.12 Coefficient of Friction Units | 5 |
| Between 0.12 and 0.14 Coefficient of Friction Units | 6 |
| Between 0.14 and 0.16 Coefficient of Friction Units | 7 |

These ratings are summed up for all cycles completed at one apply pressure and speed setting and then for the entire test. The maximum NVH rating is 9600 points (6 pressures×4 speeds×25 repeats×8 NVH Rating=4800, ×2 for pre and post durability evaluation=9600). This would be considered very poor friction performance. The minimum NVH rating is 0 points. This would be considered excellent friction performance. The Post Durability NVH rating for EX1 is 945, and 2095 for CE1.

The data obtained from the tests indicates that the lubricating composition of the invention is capable of providing a limited slip differential with a low tendency towards post durability NVH often manifested as chatter.

It is known that some of the materials described above may interact in the final formulation, so that the components of the final formulation may be different from those that are initially added. The products formed thereby, including the products formed upon employing lubricant composition of the present invention in its intended use, may not be susceptible of easy description. Nevertheless, all such modifications and reaction products are included within the scope of the present invention; the present invention encompasses lubricant composition prepared by admixing the components described above.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulphoxy);

(iii) hetero substituents, that is, substituents which, while having a predominantly hydrocarbon character, in the context of this invention, contain other than carbon in a ring or chain otherwise composed of carbon atoms; and (iv) heteroatoms include sulphur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of lubricating a limited slip differential comprising supplying to the limited slip differential a lubricating composition comprising:
    (a) about 2.3 wt % to about 2.5 wt % of zinc 2-ethylhexanoate,
    (b) a sulphur-containing compound, wherein the sulphur-containing compound comprises a dimercaptothiadiazole or derivative, or mixtures thereof, and
    (c) an oil of lubricating viscosity,
wherein the lubricating composition has a sulphur content in the range of 0.3 wt % to 5 wt %.

2. The method of claim 1, wherein the sulphur-containing compound further comprises a polysulphide, or a sulphurised olefin.

3. The method of claim 1 further comprising a phosphorus-containing compound.

4. The method of claim 3, wherein the phosphorus containing compound is an amine salt of a phosphoric acid ester.

5. The method of claim 4, wherein the amine salt of a phosphoric acid ester is a sulphur-free phosphorus-containing compound of an amine salt of either (i) a hydroxy-substituted di-ester of phosphoric acid, or (ii) a phosphorylated hydroxy-substituted di- or tri-ester of phosphoric acid.

6. The method of claim 1 further comprising a boron-containing compound.

7. The method of claim 6, wherein the boron-containing compound is a borated dispersant, a borate ester or a borated phospholipid.

* * * * *